United States Patent
Levin et al.

[11] Patent Number: 5,925,486
[45] Date of Patent: Jul. 20, 1999

[54] IMAGING MEMBERS WITH IMPROVED WEAR CHARACTERISTICS

[75] Inventors: Ronald Harold Levin; Scott Thomas Mosier, both of Boulder, Colo.

[73] Assignee: Lexmark International, Inc., Lexington, Ky.

[21] Appl. No.: 08/988,791

[22] Filed: Dec. 11, 1997

[51] Int. Cl.$^6$ .................................................. G03G 5/047
[52] U.S. Cl. .................................................................. 430/59
[58] Field of Search ...................... 430/59, 73, 74, 430/83

[56] References Cited

U.S. PATENT DOCUMENTS

| | | | |
|---|---|---|---|
| 3,441,410 | 4/1969 | Brynko . | |
| 3,451,811 | 6/1969 | Brynko . | |
| 4,150,987 | 4/1979 | Anderson | 430/59 |
| 4,256,821 | 3/1981 | Enomoto et al. | 430/59 |
| 4,284,698 | 8/1981 | Kazami et al. | 430/59 |
| 4,297,426 | 10/1981 | Sakai et al. | 430/59 |
| 4,321,318 | 3/1982 | Anderson et al. | 430/59 |
| 4,338,388 | 7/1982 | Sakai et al. | 430/59 |
| 4,362,798 | 12/1982 | Anderson et al. | 430/59 |
| 4,385,106 | 5/1983 | Sakai | 430/59 |
| 4,387,147 | 6/1983 | Sakai | 430/58 |
| 4,390,611 | 6/1983 | Ishikawa et al. | 430/59 |
| 4,413,045 | 11/1983 | Ishikawa et al. | 430/59 |
| 4,471,040 | 9/1984 | Katagiri et al. | 430/59 |
| 4,495,264 | 1/1985 | Takahashi et al. | 430/58 |
| 4,554,231 | 11/1985 | Ishikawa et al. | 430/59 |
| 4,596,754 | 6/1986 | Tsutsui et al. | 430/58 |
| 4,652,507 | 3/1987 | Dössel | 430/57 |
| 4,874,682 | 10/1989 | Scott et al. | 430/59 |
| 4,882,253 | 11/1989 | Kato et al. | 430/59 |
| 4,889,784 | 12/1989 | Champ et al. | 430/58 |
| 5,061,584 | 10/1991 | Fujimori et al. | 430/59 |
| 5,080,991 | 1/1992 | Ono et al. | 430/73 |
| 5,130,215 | 7/1992 | Adley et al. | 430/58 |
| 5,130,217 | 7/1992 | Champ et al. | 430/59 |
| 5,213,924 | 5/1993 | Sakamoto et al. | 430/58 |
| 5,284,728 | 2/1994 | Murayama et al. | 430/59 |
| 5,290,649 | 3/1994 | Suzuki et al. | 430/59 |
| 5,342,719 | 8/1994 | Pai et al. | 430/59 |
| 5,453,343 | 9/1995 | Liu et al. | 430/59 |
| B1 4,481,273 | 7/1990 | Katagiri et al. | 430/59 |

FOREIGN PATENT DOCUMENTS 31 46 072  8/1982  Germany .

*Primary Examiner*—Roland Martin
*Attorney, Agent, or Firm*—John A. Brady

[57] ABSTRACT

Benzaldehyde-based hydrazone compounds of the formula

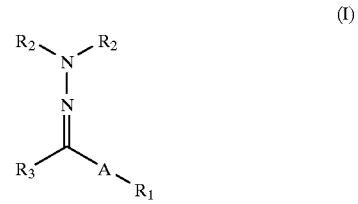

(I)

wherein A represents a monocyclic or polycyclic divalent aromatic radical including at least one hydroxy-terminated substituent; $R_1$ represents an N,N-dialkyl amino, N,N-diaryl amino or N-alkyl,N-aryl amino group; each $R_2$ independently represents an alkyl, halogen, alkoxy group or substituted or unsubstituted monocyclic or polycyclic monovalent aromatic radical, with the proviso that at least one $R_2$ is aromatic; and $R_3$ represents hydrogen, alkyl or a substituted or unsubstituted monocyclic or polycyclic monovalent aromatic radical.

18 Claims, 2 Drawing Sheets

IMAGING MEMBERS WITH IMPROVED WEAR CHARACTERISTICS

FIELD OF THE INVENTION

The present invention is directed to aldehyde-based hydrazone compounds and their use as charge transport compounds in imaging members, for example, photoconductors of electrophotographic reproduction devices.

BACKGROUND OF THE INVENTION

In electrophotography, a latent image is created on the surface of an imaging member such as a photoconducting material by selectively exposing areas of the surface to light. A difference in electrostatic charge density is created between those areas on the surface which are exposed to light and those areas on the surface which are not exposed to light. The latent electrostatic image is developed into a visible image by electrostatic toners. The toners are selectively attracted to either the exposed or unexposed portions of the photoconductor surface, depending on the relative electrostatic charges on the photoconductor surface, the development electrode and the toner.

The use of charge transport compounds or molecules in imaging members such as electrophotographic photoconductors is well known in the art. Typically, a layered electrophotographic photoconductor comprises a metal ground plane member on which a charge generation layer (CGL) and a charge transport layer (CTL) are coated. When a hole transport layer is formed on the top of the charge generation layer, the photoconductor surface typically is negatively charged. Conversely, when the charge generation layer is formed on the top of the charge transport layer, the photoconductor surface typically is positively charged. Generally, the charge generation layer comprises a polymeric binder containing a charge generation compound or molecule while the charge transport layer comprises a polymeric binder containing a charge transport compound or molecule. The charge generation compounds within the CGL are sensitive to image-forming radiation and photogenerate electron-hole pairs within the CGL as a result of such radiation. The CTL is usually transparent to the image-forming radiation and the charge transport compounds serve to transport holes to the surface of the photoconductor. Photoconductors of this type are disclosed in the Adley et al U.S. Pat. No. 5,130,215 and the Balthis et al U.S. Pat. No. 5,545,499.

The use of hydrazone compounds as charge transport compounds or molecules in a charge transport layer of a photoconductive member is also known in the art as disclosed in the Anderson et al U.S. Pat. Nos. 4,150,987 and 4,362,798, the Ishikawa et al U.S. Pat. Nos. 4,390,611 and 4,413,045, and the Sakai et al U.S. Pat. No. 4,387,147. A hydrazone compound which is commonly employed in charge transport layers comprises 4-(diethylamino) benzaldehyde diphenylhydrazone (DEH). Photoconductors having good sensitivity have been obtained with the use of hydrazone compounds such as DEH as the charge transport compound of a charge transport layer. However, as photoconductors having improved performance or extended photoconductor life are continually desired, there is a continuing need for the development of new materials to meet these demands.

SUMMARY OF THE INVENTION

Accordingly, it is an object of the present invention to provide new hydrazone compounds which are suitable, inter alia, for use as charge transport compounds in imaging members, such imaging members including, but not limited to, electrophotographic photosensitive members. It is a further object of the invention to provide new hydrazone compounds suitable for use as charge transport compounds in the charge transport layer of a photoconductor apparatus. It is another object of the invention to provide imaging members which exhibit good sensitivity and mechanical durability.

These and additional objects and advantages are provided by the aldehyde-based hydrazone compounds of the present invention which are particularly advantageous for use as charge transport compounds in imaging members. The aldehyde-based hydrazone compounds are of the following Formula (I):

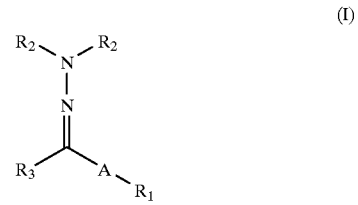

wherein A represents a monocyclic or polycyclic divalent aromatic radical including at least one hydroxy-terminated substituent; $R_1$ represents an N,N-dialkyl amino, N,N-diaryl amino or N-alkyl,N-aryl amino group; each $R_2$ independently represents an alkyl, alkoxy group or substituted or unsubstituted monocyclic or polycyclic monovalent aromatic radical, with the proviso that at least one $R_2$ is aromatic; and $R_3$ represents hydrogen, alkyl or a substituted or unsubstituted monocyclic or polycyclic monovalent aromatic radical.

The aldehyde-based hydrazone compounds according to the present invention are advantageous for use as charge transport compounds in imaging members, one embodiment of which comprises photoconductive members. Particularly, the aldehyde-based hydrazone compounds of the invention (preferably benzaldehyde-based hydrazone compounds) may be used to provide imaging members with good sensitivity and improved mechanical durability as compared with various conventional imaging devices. These and additional objects and advantages provided by the compounds and imaging members of the present invention will be further apparent in view of the following detailed description.

BRIEF DESCRIPTION OF THE DRAWING

The present invention as set forth in the detailed description will be more fully understood when viewed in connection with the drawing in which.

DETAILED DESCRIPTION

Figure 1:
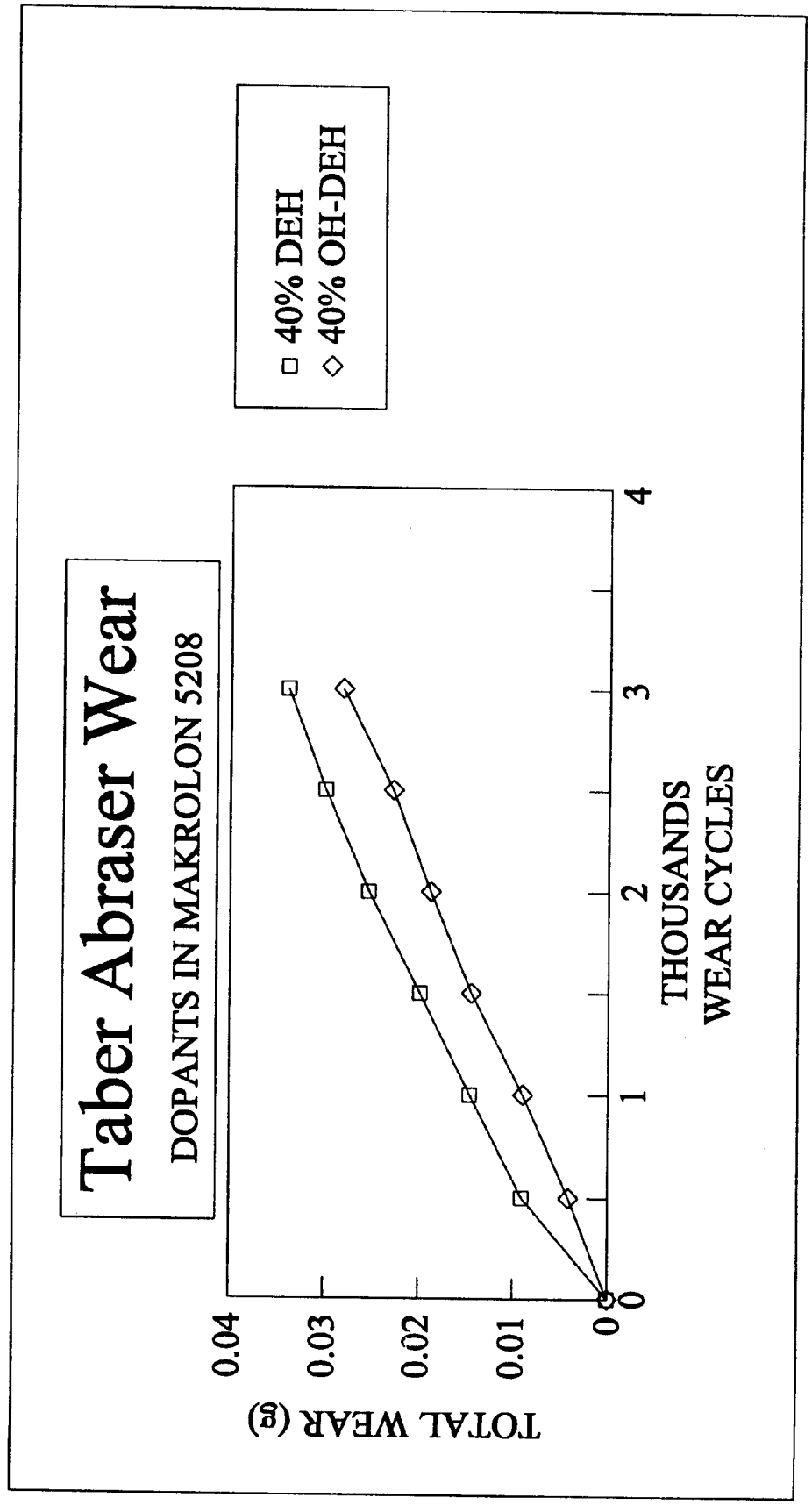
FIG. 1 sets forth wear properties of a charge transport layer employing an aldehyde-based hydrazone compound according to the present invention as compared with a charge transport layer employing a conventional hydrazone compound as described in Example 1.

The aldehyde-based hydrazone compounds according to the present invention are of the Formula (I):

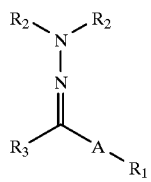

(I)

wherein A represents a monocyclic or polycyclic divalent aromatic radical including at least one hydroxy-terminated substituent; $R_1$ represents an N,N-dialkyl amino, N,N-diaryl amino or N-alkyl,N-aryl amino group; each $R_2$ independently represents an alkyl, alkoxy group or substituted or unsubstituted monocyclic or polycyclic monovalent aromatic radical, with the proviso that at least one $R_2$ is aromatic; and $R_3$ represents hydrogen, alkyl or a substituted or unsubstituted monocyclic or polycyclic monovalent aromatic radical.

In one preferred embodiment, A is a substituted or unsubstituted monocyclic or polycyclic divalent aromatic radical of the Formula (II), (III) or (IV):

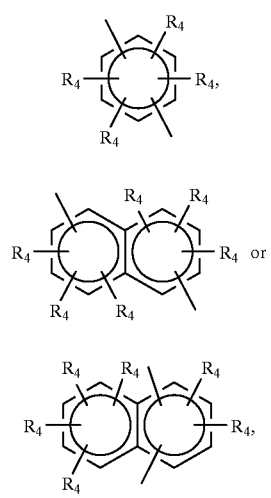

wherein at least one $R_4$ comprises a hydroxy-terminated group and each remaining $R_4$ is independently hydrogen, $C_1$–$C_6$ alkyl, a hydroxy-terminated group or a substituted or unsubstituted, monocyclic or polycyclic monovalent aromatic radical. In a preferred embodiment, the hydroxy-terminated substituent $R_4$ is of the formula —$(C(R_5)_2)_t$—OH or of the formula —$(C(R_5)_2)_t$—O—$(C(R_5)_2)_t$—OH, wherein each $R_5$ independently comprises hydrogen or an alkyl group, for example a $C_1$ to $C_6$ alkyl group, and each t is independently from 0 to 6. In a further preferred embodiment, each t is 0, 1 or 2 and each $R_5$ is independently hydrogen, methyl or ethyl. In another preferred embodiment, the hydroxy-terminated substituent $R_4$ is a hydroxy group, —OH.

When the $R_1$ substituent is attached to the aromatic ring which is linked to the remainder of the aldehyde-based compound (i.e., A is of Formula (II) or (IV)), the substituent $R_1$ may be in the ortho, meta or para position with respect to the bond attaching A to the remainder of the aldehyde-based compound. Similarly, when A is of Formula (III), the substituent $R_1$ may be in any position relative to the bond attaching A to the remainder of the aldehyde-based compound. In a further preferred embodiment, A comprises a phenyl group which, in addition to the hydroxy substituent and the substituent $R_1$, may be further substituted or unsubstituted.

As set forth above, $R_1$ represents an N,N-dialkylamino, N,N-diarylamino or N-alkyl, N-arylamino group. Preferred alkyl substituents comprise from 1 to about 6 carbon atoms. In a preferred embodiment, $R_1$ comprises an N,N-dialkylamino group or an N,N-diphenylamino group. In a further preferred embodiment, A is of Formula (II) or (IV) and $R_1$ is para to the linkage of the A group to the remainder of the aldehyde-based compound.

In a further preferred embodiment, each $R_2$ comprises a substituted or unsubstituted phenyl group, preferably of the following formula (V):

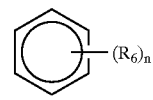

wherein n is from 0 to 5 and each $R_6$ independently represents halogen or an alkyl group, for example of from 1 to about 6 carbon atoms. In a preferred embodiment, n is 0, 1 or 2.

As set forth above, $R_3$ represents hydrogen, alkyl or a substituted or unsubstituted monocyclic or polycyclic monovalent aromatic radical. Suitable alkyl groups include from 1 to about 6 carbon atoms. Preferably, $R_3$ represents hydrogen, a $C_1$–$C_6$ alkyl group or a substituted or unsubstituted phenyl group. Suitable phenyl substituents include halogen and alkyl groups. In a further preferred embodiment, $R_3$ comprises hydrogen or a $C_1$–$C_6$ alkyl group, most preferably, hydrogen.

The aldehyde-based hydrazone compounds according to the present invention may be obtained by reacting, for example, a corresponding aldehyde (preferably benzaldehyde with a hydroxy terminated group which is most preferably a hydroxy group) with an equimolar amount of the appropriately substituted hydrazine in a suitable solvent. Alternatively, the hydrazine may be added in an excess amount to insure a complete reaction. After the reaction is completed, the hydrazone compounds can be purified by recrystallization.

$C_{1-4}$ alcohols, methyl ethyl ketone and ethyl acetate, for example, are suitable solvents. The hydrazine compounds used in this invention are commercially available from Aldrich Chemical Company, Inc. and may be prepared, for example, via art recognized condensation reactions.

The aldehyde-based hydrazone compounds of the present invention are advantageous for use as charge transport compounds in imaging members, including, but not limited to, photoconductors for use in electrophotographic reproduction devices such as copiers and printers. While specific embodiments of imaging members discussed herein comprise dual layer photoconductors, other imaging members are well known in the art and within the scope of the present invention.

Typically, the photoconductor devices in which the aldehyde-based hydrazone compounds of the present invention may be employed as charge transport materials will comprise a substrate, a charge generating layer which absorbs light and, as a result, generates electrical charge carriers, and a charge transport layer which transports the charge carriers to the exposed surface of the photoconductor.

The photoconductor substrate may be flexible, for example in the form is of a flexible web or a belt, or inflexible, for example in the form of a drum.

Typically, the photoconductor substrate is uniformly coated with a thin layer of a metal, preferably aluminum, which functions as an electrical ground plane.

In a further preferred embodiment, the aluminum is anodized to convert the aluminum surface into a thicker aluminum oxide surface. Alternatively, the ground plane member may comprise a metallic plate, such as aluminum or nickel, a metallic drum or foil, or a plastic film on which aluminum, tin oxide or indium oxide or the like is vacuum evaporated.

As set forth above, the charge generation layer may be formed on the photoconductor substrate, followed by formation of the charge transport layer, whereby the photoconductor surface is negatively charged, or, conversely, the charge transport layer may be formed on the photoconductor substrate and the charge generation layer is in turn formed on the charge transport layer, whereby the photoconductor surface is positively charged. Typically, each of the charge generation and charge transport layers comprise a polymeric binder containing the charge generation compound and charge transport compound, respectively.

Various charge generation compounds which are known in the art are suitable for use in the charge generation layers of imaging members according to the present invention. Organic charge generation compounds including disazo compounds, for example as disclosed in the Ishikawa et al U.S. Pat. No. 4,413,045, phthalocyanine dyes, including both metal-free forms such as X-form metal-free phthalocyanines and the metal-containing phthalocyanines such as titanium-containing phthalocyanines as disclosed in U.S. Pat. Nos. 4,664,997, 4,725,519 and 4,777,251, including oxo-titanyl phthalocyanine, squaric acid-derived dyes, for example hydroxy-squaraine charge generation compounds, and the like are several examples of the many well known charge generating compounds suitable for use in the present imaging members. The charge generation compounds are employed in conventional amounts suitable for providing the charge generation effects. The polymeric binder of the charge generation layer may be any polymeric binder conventionally employed in the art, including, but not limited to, vinyl polymers such as polyvinyl chloride, polyvinyl butyral and polyvinyl acetate, polycarbonate polymers, epoxy resins and copolymers, including polyester carbonates, and the like.

Similar polymers may be employed for the charge transport layer, with polycarbonate polymers and copolymers being preferred for use therein. The aldehyde-based hydrazone compounds of the present invention are included in the charge transport layer in an amount effective to provide the desired electron hole transport function. Suitably, the charge transport layer will include the aldehyde-based hydrazone compounds of the present invention in an amount of from about 20 to about 60 weight percent of the charge transport layer and more preferably in an amount of from about 30 to about 50 weight percent of the charge transport layer.

The photoconductor substrate will be a metal surface on top of which is an anodization layer typically having a thickness from about 0.01 to about 10.0 microns; preferably from about 0.05 to about 7.0 microns, and most preferably, from about 3.0 to about 5.0 microns. The charge generation layer will have a thickness of from about 0.05 to about 5.0 microns, and the charge transport layer will have a thickness of from about 10.0 to about 35.0 microns. In accordance with techniques known in the art, a barrier layer may be provided between the ground plane and the charge generation layer, typically having a thickness of from about 0.05 to about 2.0 microns. The respective charge generation layer and charge transport layer are formed by dispersing or dissolving the charge generating compound or the charge transport compound, respectively, in a polymeric binder and solvent, coating the resulting dispersion or solution, as the case may be, on the respective underlying layer and drying the coating.

Improvements and advantages provided by the aldehyde-based hydrazone compounds according to the present invention when employed as charge transport compounds in imaging members are illustrated in the examples. In the examples and throughout the present specification, parts and percentages are by weight unless otherwise specified.

EXAMPLE 1

In this example, two charge transport layers were prepared in accordance with conventional techniques and subjected to measurement of their wear properties, respectively. The charge transport layers comprised Makrolon 5208, a bisphenol-A-polycarbonate polymeric binder supplied by Bayer, Inc., and about 40 weight percent of a charge transport compound. Specifically, the charge transport layer 1A according to the present invention contained about 40 weight percent of 2-hydroxy-4-(diethylamino) benzaldehyde diphenylhydrazone while the charge transport layer 1B contained about 40 weight percent of the conventional 4-(diethylamino) benzaldehyde diphenylhydrazone (DEH).

The wear rates of these charge transport layers were measured according to a Taber abraser wear procedure, the results of which are set forth in FIG. 1 wherein total wear is shown as a function of wear cycles. The results set forth in FIG. 1 demonstrate that the charge transport layer including the hydroxy benzaldehyde-based hydrazone compound according to the present invention exhibited lower wear as compared with the charge transport layer containing the conventional DEH. Thus, the hydroxy benzaldehyde-based hydrazone compounds according to the present invention may be employed in charge transport layers to provide photoconductors with longer useful life.

EXAMPLE 2

In this example, two layer photoconductors were made in accordance with conventional techniques. The charge generation layer was formed on an aluminum drum substrate and comprised approximately 35 weight percent at hydroxy squaraine (OH-Sq) and approximately 65 weight percent of a polymeric binder comprising a mixture of polyvinyl butyral and epoxy resin[sold as (Epon 1009 from Shell Chemical) a poly(bisphenol-A-co-epichlorohydrin) glycidyl end capped]. The charge transport layer was formed on the charge generation layer. In a first photoconductor 2A, the charge transport layer comprised approximately 40 weight percent of a benzaldehyde-based hydrazone compound according to the present invention, namely 2-hydroxy-4-(diethylamino)benzaldehyde diphenylhydrazone, as the charge transport compound and approximately 60 weight percent of the Makrolon 5208 polymeric binder. In a second photoconductor 2B, the charge transport layer comprised approximately 40 weight percent of the conventional charge transport compound, DEH and about 60 weight percent of the Makrolon 5208 polymeric binder.

To determine the sensitivities of the photoconductors of this example, the photoconductors were tested using a sensitometer fitted with electrostatic probes to measure the voltage magnitude of the photoconductor's latent electrostatic image. The sensitometer included a charging source designed to charge the photoconductor to about −700 V.

Specifically, the photosensitivity was measured as the amount of light energy, in microjoules/cm², required to reduce the photoconductor's voltage from its initial charge of about −700 V to about −150 to −200 V. The results of these measurements are set forth in FIG. 2.

Figure 2:
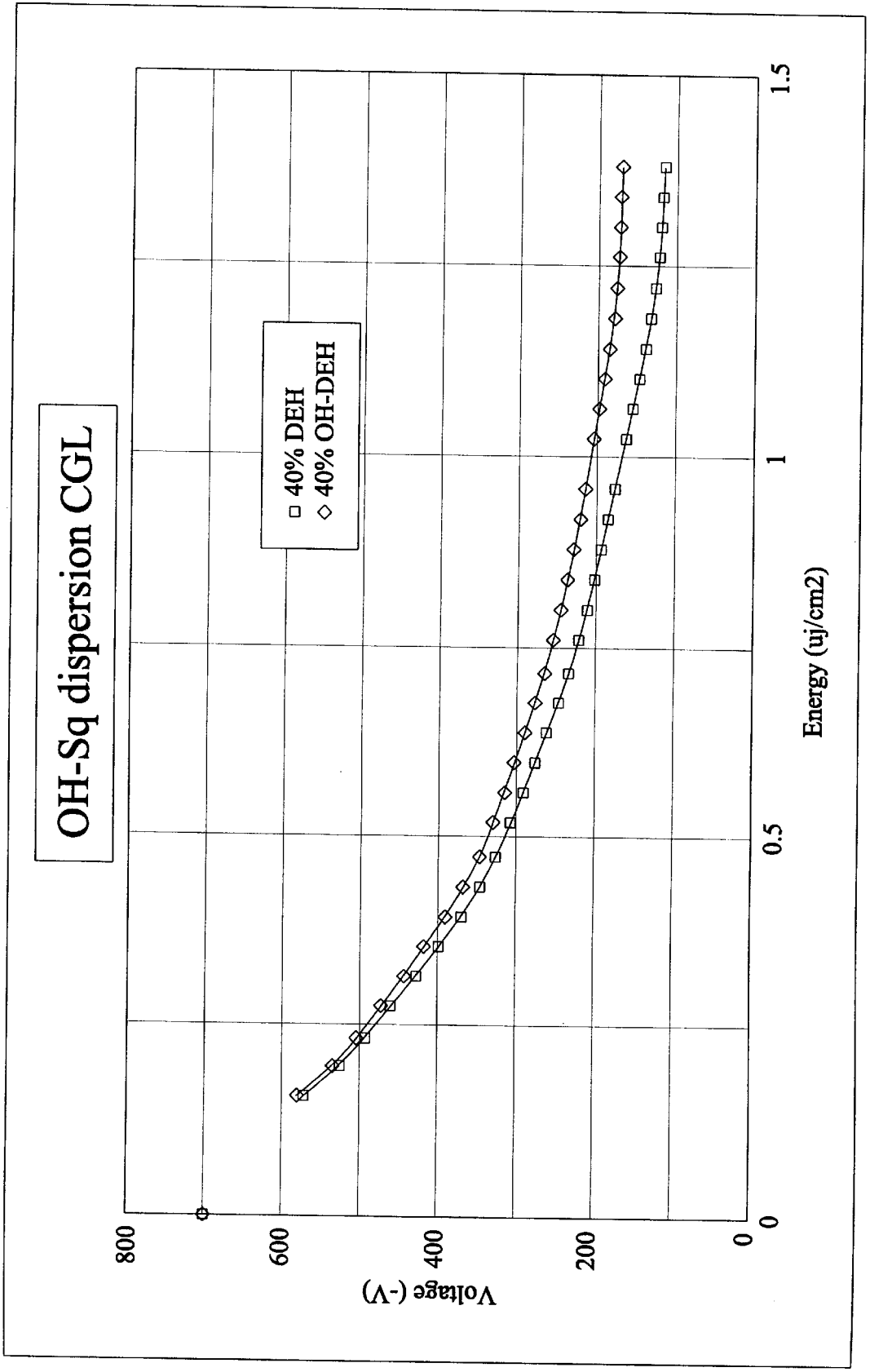
FIG. 2 sets forth the sensitivities of a photoconductor comprising an aldehyde-based hydrazone compound according to the present invention as compared with a photoconductor comprising a conventional hydrazone compound as described in Example 2.

The results in FIG. 2 demonstrate that the photoconductor 2A containing the benzaldehyde-based hydrazone compound of the present invention as the charge transport compound in the charge transport layer exhibited comparable sensitivity as compared with the photoconductor 2B containing the conventional DEH as the charge transport compound in the charge transport layer. Thus, the benzaldehyde-based hydrazone compounds according to the present invention may be used to produce photoconductors which exhibit good sensitivity and increased wear resistance, whereby longer useful photoconductor life may be achieved.

The foregoing examples and various preferred embodiments of the present invention set forth herein are provided for illustrative purposes only and are not intended to limit the scope of the invention defined by the claims. Additional embodiments of the present invention and advantages thereof will be apparent to one of ordinary skill in the art and are within the scope of the invention defined by the following claims.

We claim:

1. An imaging member comprising a charge generation layer and a charge transport layer wherein the improvement comprises said charge transport layer containing a charge transport compound of the formula within A is

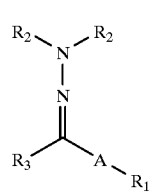

(I)

a monocyclic or polycyclic divalent aromatic radical including at least one hydroxy-terminated substituent; $R_1$ is an N,N-dialkyl amino, N,N-diaryl amino or N-alkyl,N-aryl amino group; each $R_2$ independently is an alkyl, alkoxy group or substituted or unsubstituted monocyclic or polycyclic monovalent aromatic radical, with the proviso that at least one $R_2$ is aromatic; and $R_3$ is hydrogen, alkyl or a substituted or unsubstituted monocyclic or polycyclic monovalent aromatic radical.

2. An imaging member according to claim 1, wherein A is of the formula

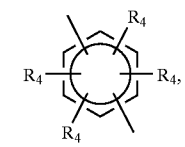

(II)

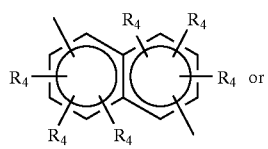

(III)

-continued

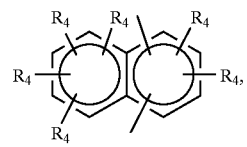

(IV)

wherein at least one $R_4$ is a hydroxy-terminated group and each remaining $R_4$ independently is hydrogen, $C_1$–$C_6$ alkyl, a hydroxy-terminated group or a substituted or unsubstituted, monocyclic or polycyclic monovalent aromatic radical.

3. An imaging member according to claim 1, wherein A is a phenylene group having at least one hydroxy-terminated group of the formula —$(C(R_5)_2)_t$—OH or of the formula —$(C(R_5)_2)_t$—O—$(C(R_5)_2)_t$—OH, wherein each $R_5$ independently is hydrogen or a $C_1$–$C_6$ alkyl and each t independently is from 0 to 6.

4. An imaging member according to claim 3, wherein A is a divalent phenolic group.

5. An imaging member according to claim 1, wherein $R_1$ is an N,N-dialkyl amino group.

6. An imaging member according to claim 4, wherein $R_1$ is an N,N-diethyl amino group.

7. An imaging member according to claim 1, wherein $R_3$ is hydrogen.

8. An imaging member according to claim 1, wherein A is a phenolic group, $R_1$ is an N,N-dialkyl amino group, and $R_3$ is hydrogen.

9. An imaging member according to claim 8, wherein at least one $R_2$ comprises a substituted or unsubstituted phenyl group.

10. An imaging member according to claim 1, wherein said charge transport layer which from about 20 to about 60 weight percent of the charge transport compound.

11. An imaging member according to claim 10, wherein the charge transport layer further includes a polymeric binder.

12. An imaging member according to claim 11, wherein the polymeric binder is a polycarbonate polymer or copolymer.

13. An imaging member according to claim 1, wherein said charge generating layer is a squaraine charge generating material in a polymeric binder.

14. An imaging member according to claim 1, comprising a ground plane member, said charge generation layer on the ground plane member, and said charge transport layer on the charge generation layer.

15. An imaging member according to claim 1, comprising a ground plane member, said charge transport layer on the ground plane member, and said charge generation layer on the charge transport layer.

16. An imaging member, comprising an aluminum ground plane member, a charge generation layer on the ground plane member, and a charge transport layer on the charge generation layer, wherein the charge transport layer comprises a polymeric binder and from about 20 to about 60 weight percent of a charge transport compound of the formula

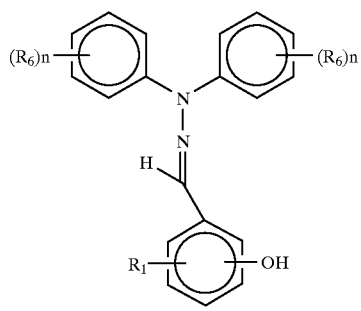
wherein $R_1$ is an N,N-dialkyl amino, N,N-diaryl amino or N-alkyl, N-aryl amino group, each n is independently from 0 to 5 and each $R_6$ independently is halogen or an alkyl group.
17. An imaging member according to claim 16, wherein $R_1$ is N,N-dialkylamino.
18. An imaging member according to claim 17, wherein $R_1$ is in the para position and the hydroxy group is in the ortho position.
* * * * *